US008735543B2

(12) United States Patent
Andersson et al.

(10) Patent No.: US 8,735,543 B2
(45) Date of Patent: May 27, 2014

(54) CHIMERIC MOMP ANTIGEN

(75) Inventors: Sören Andersson, Örebro (SE); Åke Strid, Örebro (SE)

(73) Assignee: Spixia Biotechnology AB, Örebro (SE)

( * ) Notice: Subject to any disclaimer, the term of this patent is extended or adjusted under 35 U.S.C. 154(b) by 0 days.

(21) Appl. No.: 13/700,662

(22) PCT Filed: May 27, 2011

(86) PCT No.: PCT/EP2011/058755

§ 371 (c)(1),
(2), (4) Date: Nov. 28, 2012

(87) PCT Pub. No.: WO2011/147975

PCT Pub. Date: Dec. 1, 2011

(65) Prior Publication Data

US 2013/0156805 A1 Jun. 20, 2013

(30) Foreign Application Priority Data

May 28, 2010 (SE) ....................................... 1050535

(51) Int. Cl.

| | |
|---|---|
| ***A61K 39/00*** | (2006.01) |
| ***A61K 39/118*** | (2006.01) |
| ***C07H 21/04*** | (2006.01) |
| ***C07K 1/00*** | (2006.01) |
| ***C12N 1/20*** | (2006.01) |
| ***C12N 15/00*** | (2006.01) |
| ***C12P 21/06*** | (2006.01) |

(52) U.S. Cl.
USPC ...... 530/350; 536/23.7; 435/69.1; 435/252.3; 435/320.1; 424/185.1; 424/263.1

(58) Field of Classification Search
None
See application file for complete search history.

(56) References Cited

U.S. PATENT DOCUMENTS

| | | | |
|---|---|---|---|
| 6,235,290 | B1 | 5/2001 | Brunham |
| 6,344,202 | B1 | 2/2002 | Brunham |
| 6,696,421 | B2 | 2/2004 | Brunham |
| 6,838,085 | B2 | 1/2005 | Brunham |
| 7,063,853 | B1 | 6/2006 | Brunham |
| 7,220,423 | B2 | 5/2007 | Brunham |
| 2001/0041788 | A1 | 11/2001 | DeMars et al. |
| 2005/0232941 | A1 | 10/2005 | Bhatia et al. |
| 2008/0075717 | A1 | 3/2008 | Tranchand-Bunel |
| 2009/0022755 | A1 | 1/2009 | Barth et al. |

FOREIGN PATENT DOCUMENTS

| | | |
|---|---|---|
| EP | 0915978 | 5/1999 |
| EP | 1587825 | 10/2005 |
| EP | 1868641 | 12/2007 |
| FR | 2850384 | 7/2004 |
| JP | 10-234395 | 9/1998 |
| JP | 4249279 | 2/2009 |
| WO | 94/06827 | 3/1994 |
| WO | 95/11998 | 5/1995 |
| WO | 95/12411 | 5/1995 |
| WO | 96/31236 | 10/1996 |
| WO | 97/06263 | 2/1997 |
| WO | 98/02546 | 1/1998 |
| WO | 98/10789 | 3/1998 |
| WO | 98/28005 | 7/1998 |
| WO | 99/51745 | 10/1999 |
| WO | 2004/069140 | 8/2004 |
| WO | 2006/045308 | 5/2006 |
| WO | 2006/104890 | 10/2006 |
| WO | 2007/027954 | 3/2007 |
| WO | 2007/134385 | 11/2007 |
| WO | 2008/040757 | 4/2008 |

OTHER PUBLICATIONS

Ortiz et al., "T-cell epitopes in variable segments of *Chlamydia trachomatis* major outer membrane protein elicit serovar-specific immune responses in infected humans," Infection and Immunity, 2001, vol. 68, No. 3,pp. 1719-1723.

Klein et al., "Detection of *Chlamydia pneumoniae*-specific antibodies binding to the VD2 and VD3 regions of the major outer membrane protein," Journal of Clinical Microbiology, 2003, vol. 41, No. 5, pp. 1957-1962.

Murdin et al., "Poliovirus hybrids expressing neutralization epitopes from variable domains I and IV of the major outer membrane protein of *Chlamydia trachomatis* elicit broadly cross-reactive *C. trachomatis*-neutralizing antibodies," Infection and Immunity, 1995, vol. 63, No. 3, p. 1116-1121.

Kalbina et al., "A novel chimeric MOMP antigen expressed in *Escherichia coli, Arabidopsis thaliana*, and *Daucus carota* as a potenial *Chlamydia trachomatis* vaccine candidate," Protein Expression and Purification, 2001, vol. 80, pp. 194-202.

Findlay et al., "Surface expression, single-channel analysis and membrane topology of recombinant *Chlamydia trachomatis* major outer membrane protein," BMC Microbiology, 2005, vol. 5, No. 5, doi:10.1186/1471-2180/5/5, 15 pages total.

Faros et al., "CD4$^+$ T cells and antibody are required for optimal major outer membrane protein vaccine-induced immunity to *Chlamydia muridarum* genital infection," Infection and Immunity, 2010, vol. 78, No. 10, pp. 4374-4383.

Farris et al., "Vaccination against *Chlamydia* genital infection utilizing the Murine *C. muridarum* Model," Infection and Immunity, 2011, vol. 79, No. 3, pp. 986-996.

(Continued)

*Primary Examiner* — Albert Navarro

(74) *Attorney, Agent, or Firm* — Hamre, Schumann, Mueller & Larson, P.C.

(57) ABSTRACT

The present invention regards polypeptides capable of eliciting an immunological response that is protective against *Chlamydia trachomatis*. The polypeptide comprises a first amino acid sequence which has at least 90% homology with the amino acid sequence according to SEQ ID NO: 1 and a second amino acid sequence which has at least 90% homology with the amino acid sequence according to SEQ ID NO: 2. Furthermore, production of these polypeptides and pharmaceutical compositions comprising them are also provided.

20 Claims, 11 Drawing Sheets

(56) References Cited

OTHER PUBLICATIONS

Schautteet et al., "Protection of pigs against gentital *Chlamydia trachomatis* challenge by parenteral or mucosal DNA immunization," Vaccine, 2012, vol. 30, pp. 2869-2881.

Schautteet et al., "Protection of pigs against *Chlamydia trachomatis* challenge by administration of a MOMP-based DNA vaccine in the vaginal mucosa," Vaccine, 2011, vol. 29, pp. 1399-1407.

Schautteet et al., "*Chlamydia trachmatis* vaccine research through the years," Infectious Diseases in Obstetrics and Gynecology, vol. 2011, Article ID 963513, 9 pages total.

Xu et al., "Protective immunity against *Chlamydia trachomatis* genital infection induced by a vaccine based on the major outer membrane multi-epitope human papillomavirus major capsid protein L1," Vaccine, 2011, vol. 29, pp. 2672-2678.

Zhu et al., "Identification of immunodominant linear B-cell epitopes within the major outer membrane protein of *Chlamydia trachomatis*," Acta Biochim Biophys Sin, 2010, vol. 42, issue 11, pp. 771-778.

O'Meara et al., "Immunization with a MOMP-based vaccine protects mice against a pulmonary *Chlamydia* challenge and identifies a disconnection between infection and pathology—Manuscript Draft—" PLOS ONE, presented 2012, 40 pages total.

```
                              SEQUENCE LISTING

<160> NUMBER OF SEQ ID NOS: 26

<210> SEQ ID NO 1
<211> LENGTH: 27
<212> TYPE: PRT
<213> ORGANISM: Chlamydia trachomatis

<400> SEQUENCE: 1

Met Gly Asp Asn Glu Asn Gln Ser Thr Val Lys Thr Asn Ser Val Pro
1               5                   10                  15

Asn Met Ser Leu Asp Gln Ser Val Val Glu Leu
            20                  25


<210> SEQ ID NO 2
<211> LENGTH: 75
<212> TYPE: PRT
<213> ORGANISM: Chlamydia trachomatis

<400> SEQUENCE: 2

Trp Gln Ala Ser Leu Ala Leu Ser Tyr Arg Leu Asn Met Phe Thr Pro
1               5                   10                  15

Tyr Ile Gly Val Lys Trp Ser Arg Ala Ser Phe Asp Ala Asp Thr Ile
            20                  25                  30

Arg Ile Ala Gln Pro Lys Ser Ala Thr Ala Ile Phe Asp Thr Thr Thr
        35                  40                  45

Leu Asn Pro Thr Ile Ala Gly Ala Gly Asp Val Lys Ala Ser Ala Glu
    50                  55                  60

Gly Gln Leu Gly Asp Thr Met Gln Ile Val Ser
65                  70                  75


<210> SEQ ID NO 3
<211> LENGTH: 116
<212> TYPE: PRT
<213> ORGANISM: Chlamydia trachomatis

<400> SEQUENCE: 3

Met Gly Asp Asn Glu Asn Gln Ser Thr Val Lys Thr Asn Ser Val Pro
1               5                   10                  15

Asn Met Ser Leu Asp Gln Ser Val Val Glu Leu Gly Gly Gly Gly Ser
            20                  25                  30

Gly Gly Gly Gly Ser Gly Gly Gly Gly Trp Gln Ala Ser Leu Ala Leu
        35                  40                  45

Ser Tyr Arg Leu Asn Met Phe Thr Pro Tyr Ile Gly Val Lys Trp Ser
    50                  55                  60

Arg Ala Ser Phe Asp Ala Asp Thr Ile Arg Ile Ala Gln Pro Lys Ser
65                  70                  75                  80

Ala Thr Ala Ile Phe Asp Thr Thr Thr Leu Asn Pro Thr Ile Ala Gly
                85                  90                  95
```

```
Ala Gly Asp Val Lys Ala Ser Ala Glu Gly Gln Leu Gly Asp Thr Met
            100                 105                 110

Gln Ile Val Ser
        115


<210> SEQ ID NO 4
<211> LENGTH: 14
<212> TYPE: PRT
<213> ORGANISM: Artificial
<220> FEATURE:
<223> OTHER INFORMATION: V5 tag

<400> SEQUENCE: 4

Gly Lys Pro Ile Pro Asn Pro Leu Leu Gly Leu Asp Ser Thr
1               5                   10


<210> SEQ ID NO 5
<211> LENGTH: 6
<212> TYPE: PRT
<213> ORGANISM: Artificial
<220> FEATURE:
<223> OTHER INFORMATION: His tag

<400> SEQUENCE: 5

His His His His His His
1               5


<210> SEQ ID NO 6
<211> LENGTH: 148
<212> TYPE: PRT
<213> ORGANISM: Chlamydia trachomatis

<400> SEQUENCE: 6

Met Gly Asp Asn Glu Asn Gln Ser Thr Val Lys Thr Asn Ser Val Pro
1               5                   10                  15

Asn Met Ser Leu Asp Gln Ser Val Val Glu Leu Gly Gly Gly Gly Ser
            20                  25                  30

Gly Gly Gly Gly Ser Gly Gly Gly Gly Trp Gln Ala Ser Leu Ala Leu
        35                  40                  45

Ser Tyr Arg Leu Asn Met Phe Thr Pro Tyr Ile Gly Val Lys Trp Ser
    50                  55                  60

Arg Ala Ser Phe Asp Ala Asp Thr Ile Arg Ile Ala Gln Pro Lys Ser
65                  70                  75                  80

Ala Thr Ala Ile Phe Asp Thr Thr Thr Leu Asn Pro Thr Ile Ala Gly
                85                  90                  95

Ala Gly Asp Val Lys Ala Ser Ala Glu Gly Gln Leu Gly Asp Thr Met
            100                 105                 110

Gln Ile Val Ser Lys Gly Glu Leu Asn Ser Lys Leu Glu Gly Lys Pro
        115                 120                 125

Ile Pro Asn Pro Leu Leu Gly Leu Asp Ser Thr Arg Thr Gly His His
    130                 135                 140

His His His His
145


<210> SEQ ID NO 7
<211> LENGTH: 81
<212> TYPE: DNA
<213> ORGANISM: Chlamydia trachomatis
```

-continued

<400> SEQUENCE: 7
atgggagata atgaaaatca aagcacggtc aaaacgaatt ctgtaccaaa tatgagctta 60
gatcaatctg ttgttgaact t 81

<210> SEQ ID NO 8
<211> LENGTH: 225
<212> TYPE: DNA
<213> ORGANISM: Chlamydia trachomatis

<400> SEQUENCE: 8
tggcaagcaa gtttagctct ctcttacaga ttgaatatgt tcactcccta cattggagtt 60
aaatggtctc gagcaagttt tgatgccgat acgattcgta tagcccagcc aaaatcagct 120
acagctatct ttgatactac cacgcttaac ccaactattg ctggagctgg cgatgtgaaa 180
gctagcgcag agggtcagct cggagatacc atgcaaatcg tctcc 225

<210> SEQ ID NO 9
<211> LENGTH: 348
<212> TYPE: DNA
<213> ORGANISM: Chalmydia trachomatis

<400> SEQUENCE: 9
atgggagata atgaaaatca aagcacggtc aaaacgaatt ctgtaccaaa tatgagctta 60
gatcaatctg ttgttgaact tggtggaggc ggttcaggcg gaggtggatc cggcggtggc 120
ggatggcaag caagtttagc tctctcttac agattgaata tgttcactcc ctacattgga 180
gttaaatggt ctcgagcaag ttttgatgcc gatacgattc gtatagccca gccaaaatca 240
gctacagcta tctttgatac taccacgctt aacccaacta ttgctggagc tggcgatgtg 300
aaagctagcg cagagggtca gctcggagat accatgcaaa tcgtctcc 348

<210> SEQ ID NO 10
<211> LENGTH: 23
<212> TYPE: DNA
<213> ORGANISM: Artificial
<220> FEATURE:
<223> OTHER INFORMATION: VS2 primer, forward 1

<400> SEQUENCE: 10
tatttgggat cgctttgatg tat 23

<210> SEQ ID NO 11
<211> LENGTH: 23
<212> TYPE: DNA
<213> ORGANISM: Artificial
<220> FEATURE:
<223> OTHER INFORMATION: VS2 primer, back 1

<400> SEQUENCE: 11
tattggaaag aagcccctaa agt 23

<210> SEQ ID NO 12
<211> LENGTH: 23
<212> TYPE: DNA
<213> ORGANISM: Artificial
<220> FEATURE:
<223> OTHER INFORMATION: VS4 primer, forward 1

<400> SEQUENCE: 12
ctcttgcact catagcagga act 23

<210> SEQ ID NO 13
<211> LENGTH: 23
<212> TYPE: DNA
<213> ORGANISM: Artificial
<220> FEATURE:
<223> OTHER INFORMATION: VS4 primer, back 1

<400> SEQUENCE: 13
tgtaactgcg tatttgtctg cat 23

<210> SEQ ID NO 14
<211> LENGTH: 21
<212> TYPE: DNA
<213> ORGANISM: Artificial
<220> FEATURE:
<223> OTHER INFORMATION: VS2 primer, forward 2&3

<400> SEQUENCE: 14
caccatggga gataatgaaa a 21

<210> SEQ ID NO 15
<211> LENGTH: 57
<212> TYPE: DNA
<213> ORGANISM: Artificial
<220> FEATURE:
<223> OTHER INFORMATION: VS2 primer, back 2

<400> SEQUENCE: 15
ccgccggatc cacctccgcc tgaaccgcct ccaccaagtt caacaacaga ttgatct 57

<210> SEQ ID NO 16
<211> LENGTH: 53
<212> TYPE: DNA
<213> ORGANISM: Artificial
<220> FEATURE:
<223> OTHER INFORMATION: VS4 primer, forward 2

<400> SEQUENCE: 16
caggcggagg tggatccggc ggtggcggat ggcaagcaag tttagctctc tct 53

<210> SEQ ID NO 17
<211> LENGTH: 20
<212> TYPE: DNA
<213> ORGANISM: Artificial
<220> FEATURE:
<223> OTHER INFORMATION: VS4 primer, back 2&3

<400> SEQUENCE: 17
ggagacgatt tgcatggtat 20

<210> SEQ ID NO 18
<211> LENGTH: 21
<212> TYPE: DNA
<213> ORGANISM: Artificial
<220> FEATURE:
<223> OTHER INFORMATION: VS4 primer back,STOP

<400> SEQUENCE: 18
attgagctcg cctcaggaga c 21

<210> SEQ ID NO 19
<211> LENGTH: 45
<212> TYPE: DNA
<213> ORGANISM: Artificial
<220> FEATURE:
<223> OTHER INFORMATION: Linker sequence

```
<400> SEQUENCE: 19

ggtggaggcg gttcaggcgg aggtggatcc ggcggtggcg gatgg                      45


<210> SEQ ID NO 20
<211> LENGTH: 15
<212> TYPE: PRT
<213> ORGANISM: Artificial
<220> FEATURE:
<223> OTHER INFORMATION: Linker sequence

<400> SEQUENCE: 20

Gly Gly Gly Gly Ser Gly Gly Gly Gly Ser Gly Gly Gly Gly Ser
1               5                   10                  15


<210> SEQ ID NO 21
<211> LENGTH: 26
<212> TYPE: PRT
<213> ORGANISM: Chlamydia trachomatis

<400> SEQUENCE: 21

Gly Asp Asn Glu Asn Gln Ser Thr Val Lys Thr Asn Ser Val Pro Asn
1               5                   10                  15

Met Ser Leu Asp Gln Ser Val Val Glu Leu
            20                  25


<210> SEQ ID NO 22
<211> LENGTH: 73
<212> TYPE: PRT
<213> ORGANISM: Chlamydia trachomatis

<400> SEQUENCE: 22

Ala Ser Leu Ala Leu Ala Tyr Arg Leu Asn Met Phe Thr Pro Tyr Ile
1               5                   10                  15

Gly Val Lys Trp Ser Arg Ala Ser Phe Asp Ala Asp Thr Ile Arg Ile
            20                  25                  30

Ala Gln Pro Lys Ser Ala Thr Ala Ile Phe Asp Thr Thr Thr Leu Asn
        35                  40                  45

Pro Thr Ile Ala Gly Ala Gly Asp Val Lys Ala Ser Ala Glu Gly Gln
    50                  55                  60

Leu Gly Asp Thr Met Gln Ile Val Ser
65                  70


<210> SEQ ID NO 23
<211> LENGTH: 26
<212> TYPE: PRT
<213> ORGANISM: Chlamydia trachomatis

<400> SEQUENCE: 23

Gly Asp Asn Glu Asn Gln Lys Thr Val Lys Ala Glu Ser Val Pro Asn
1               5                   10                  15

Met Ser Phe Asp Gln Ser Val Val Glu Leu
            20                  25


<210> SEQ ID NO 24
<211> LENGTH: 73
<212> TYPE: PRT
<213> ORGANISM: Chlamydia trachomatis
```

-continued

```
<400> SEQUENCE: 24

Ala Ser Leu Ala Leu Ala Tyr Arg Leu Asn Met Phe Thr Pro Tyr Ile
1               5                   10                  15

Gly Val Lys Trp Ser Arg Ala Ser Phe Asp Ala Asp Thr Ile Arg Ile
            20                  25                  30

Ala Gln Pro Lys Ser Ala Thr Ala Ile Phe Asp Thr Thr Thr Leu Asn
        35                  40                  45

Pro Thr Ile Ala Gly Ala Gly Asp Val Lys Thr Gly Ala Glu Gly Gln
    50                  55                  60

Leu Gly Asp Thr Met Gln Ile Val Ser
65                  70


<210> SEQ ID NO 25
<211> LENGTH: 42
<212> TYPE: DNA
<213> ORGANISM: Artificial
<220> FEATURE:
<223> OTHER INFORMATION: Linker sequence

<400> SEQUENCE: 25

ggtggaggcg gttcaggcgg aggtggatcc ggcggtggcg ga                        42


<210> SEQ ID NO 26
<211> LENGTH: 14
<212> TYPE: PRT
<213> ORGANISM: Artificial
<220> FEATURE:
<223> OTHER INFORMATION: Linker sequence

<400> SEQUENCE: 26

Gly Gly Gly Gly Ser Gly Gly Gly Gly Ser Gly Gly Gly Gly
1               5                   10
```

CHIMERIC MOMP ANTIGEN

TECHNICAL FIELD

This invention pertains in general to the field of polypeptides capable of eliciting an immunological response that is protective against *Chlamydia trachomatis*. More particularly the invention relates the production of these polypeptides and to pharmaceutical compositions comprising them.

BACKGROUND

It is known that one of the proteins forming the outer membrane complex of *Chlamydia trachomatis*, the major outer membrane protein (MOMP), is able to induce both T-cell responses and neutralizing antibodies against chlamydial infection in mammals, such as humans. A schematic overview of the MOMP protein is shown in FIG. 1, adapted from Findlay H E, McClafferty H & Ashley R H (2005) Surface expression, single-channel analysis and membrane topology of recombinant *Chlamydia trachomatis* major outer membrane protein. BMC Microbiology 5, 5, an article in which the topology of the MOMP protein was elucidated. In FIG. 1, A denotes the cell membrane and B denotes the outer surface of the cell membrane.

Use of the total MOMP protein as a vaccine against *Chlamydia trachomatis* has been disclosed in WO 2008/040757 A1.

However, animal experiments have shown very limited success of anti-chlamydial MOMP subunit vaccines. Furthermore, the production of the whole MOMP protein is tedious and expensive, not to mention limited to certain specific production methods.

To overcome the abovementioned deficiency, it has been suggested to use synthetic peptides, which combine specific epitopes from *Chlamydia trachomatis,* which epitopes trigger an immune response.

However, such isolated epitopes may not be functional in a synthetic context and thus not provide the desired effect.

Hence, an improved polypeptide for producing an immune response which is protective against *Chlamydia trachomatis* would be advantageous and in particular a polypeptide allowing for increased flexibility, cost-effectiveness, simplicity of production and purification with retained or improved immunological effect would be advantageous.

SUMMARY

Accordingly, the present invention preferably seeks to mitigate, alleviate or eliminate one or more of the above-identified deficiencies in the art and disadvantages singly or in any combination and solves at least the above mentioned problems by providing a polypeptide according to the appended patent claims.

The general solution according to the invention is to provide a polypeptide which is easy to produce and purify, but has retained capacity for producing an immune response against *Chlamydia trachomatis.*

Thus, according to a first aspect, a polypeptide is provided. Said polypeptide comprises a first amino acid sequence which has at least 90%, such as at least 95%, homology (% identity) with the amino acid sequence according to SEQ ID NO: 1, as measured with the BLAST algorithm with standard settings and a second amino acid sequence which has at least 90%, such as at least 95%, homology with the amino acid sequence according to SEQ ID NO: 2, as measured with the BLAST algorithm with standard settings, wherein said first and second amino acid sequences are separated by less than 30 amino acid residues. Said first and second amino acid sequences each comprises epitopes for producing an antigen-specific immune response which is protective against *Chlamydia trachomatis*, and a part of the membrane spanning part of the major outer membrane protein (MOMP) of *Chlamydia trachomati*. Together, the first and second amino acid sequences comprise about 25 epitopes, which may both stimulate T cell response (CD4+ and CD8+) as well as B cell response. An advantage with this is that the polypeptide is easier to produce in purified form compared to the whole MOMP protein, while still eliciting an acceptable immunological response. An advantage with the polypeptides, each comprising a part of the membrane spanning part of MOMP is that the three dimensional structure of the epitopes is conserved, since the two membrane spanning parts may interact to form a hydrophobic structure, as illustrated in FIG. 14. Another advantage with the polypeptide comprising a part of the membrane spanning part of MOMP is that the epitopes are retained in the construct during production. A further advantage with this is that it provides the possibility for hydrophobic interaction between the two parts of the chimera, in turn providing a three dimensional domain that could mimic antigenic features of the whole MOMP protein. Thus, by removing most of the membrane part of the MOMP protein from the polypeptide according to the first aspect, a polypeptide which is easier to handle than wild-type MOMP is obtained; and by simultaneously keeping specifically selected, minimal parts of the membrane helices at the ends of the sequences, a polypeptide that is more stable and may be more effective than shorter artificial sequences is obtained.

Taken together, the polypeptide provides an alternative synthetic peptide based on the MOMP protein that is antigenic and suitable for use as a vaccine.

Specifically, the polypeptide may enable retained or improved antigenicity compared to artificial, shorter sequences with only two linked epitopes, while being easy to produce and purify compared to wild-type MOMP.

In an embodiment, the polypeptide is between 107 and 132 amino acids long, such as between 107 and 112 amino acids long. An advantage with this is that the polypeptide is easier to express.

In an embodiment, the first amino acid sequence and the second amino acid sequence are separated by a linker according to SEQ ID NO: 20 or SEQ ID NO: 26.

This is advantageous, since the linker according to SEQ ID NO: 20 or SEQ ID NO: 26 is flexible, which means that it provides a possibility for interaction at random between the two parts of the chimera, increasing the probability for formation of three-dimensional structure that would be recognized by the immune system, without locking the protein in an unfavorable conformation.

Another advantage with a flexible linker is that it provides the opportunity for the two parts of the polypeptide to interact with different parts of the immune system at the same time, since they may move in relation to each other, as illustrated in FIG. 15.

In an embodiment, the epitopes for producing an antigen-specific immune response which is protective against *Chlamydia trachomatis* are conserved in several serovars of *Chlamydia trachomatis.*

This is advantageous, since it enables a protective response against more than one serovar of *Chlamydia trachomatis.*

In an embodiment, the first and second amino acid sequence is a sequence according to SEQ ID NO: 21 and SEQ ID NO: 22, respectively (*Chlamydia trachomatis*, serovar E). In another embodiment, the first and second amino acid sequence is a sequence according to SEQ ID NO: 23 and SEQ ID NO: 24, respectively (*Chlamydia trachomatis*, serovar D). The first and second amino acid sequences may also be combined from different serovars.

This is advantageous, since it enables a protective response against more than one serovar of *Chlamydia trachomatis*.

In an embodiment, the polypeptide has at least 90%, such as at least 95%, homology with the amino acid sequence according to SEQ ID NO: 3, as measured with the BLAST algorithm with standard settings. In an embodiment, the polypeptide comprises an amino acid sequence according to SEQ ID NO: 3 and in another embodiment, the polypeptide has an amino acid sequence according to SEQ ID NO: 3.

In an embodiment the polypeptide is fused to an amino acid sequence comprising a His tag according to SEQ ID NO: 5 and/or a V5 tag according to SEQ ID NO: 4.

An advantage with this is that the polypeptide is easier to purify.

In an embodiment the polypeptide has, i.e. consists of, an amino acid sequence according to SEQ ID NO: 6.

According to a second aspect, a compound comprising the amino acid sequence according to the first aspect is provided.

According to a third aspect, a nucleic acid is provided which encodes a polypeptide according to the first aspect.

In an embodiment, the nucleic acid has a first nucleic acid sequence which has at least 60%, or at least 70%, such as at least 80%, or preferably at least 90% homology, as measured with a BLAST algorithm with standard settings, with the nucleic acid sequence according to SEQ ID NO: 7 and a second nucleic acid sequence which has at least 60%, or at least 70%, such as at least 80%, or preferably at least 90% homology, as measured with a BLAST algorithm with standard settings, with the nucleic acid sequence according to SEQ ID NO: 8, wherein said first and second nucleic acid sequences are separated by less than 90 nucleic acid residues.

In an embodiment, the nucleic acid comprises a nucleic acid sequence according to SEQ ID NO: 9.

According to a fourth aspect, a plasmid is provided which comprises the nucleic acid according to the third aspect.

In an embodiment, the plasmid is used as an expression vector.

According to a fifth aspect, a cell transformed with an expression vector according to the fourth aspect is provided.

In an embodiment, the cell is chosen from the group consisting of a plant cell, a bacterium, a yeast cell, a fungi cell, an insect cell or a mammalian cell.

According to a sixth aspect, a process is provided for producing a polypeptide according to the first aspect, which process comprises culturing a cell according to the fifth aspect and recovering the polypeptide.

According to a seventh aspect, a composition is provided comprising a polypeptide according to the first aspect together with a pharmaceutically acceptable excipient.

In an embodiment, the composition further comprises an adjuvant, such as cholera toxin (CT) adjuvant.

According to an eight aspect, a polypeptide according to the first aspect, a compound according the second aspect, or a composition according to the seventh aspect for use as a medicament is provided.

According to a ninth aspect, a polypeptide according to the first aspect, a compound according the second aspect, or a composition according to the seventh aspect for use as a vaccine against *Chlamydia trachomatis* is provided.

According to a tenth aspect, a polypeptide according to the first aspect, a compound according the second aspect, or a composition according to the seventh aspect for use to prohibit infertility as a result of infection with *Chlamydia trachomatis* is provided.

According to an eleventh aspect, use is provided, wherein said polypeptide according to the first aspect, said compound according to the second aspect, or said composition according to the seventh aspect is administered orally, parenterally, by inhalation spray, topically, rectally, nasally, buccally, sublingually or vaginally.

In an embodiment, said administration is nasal administration. The nasal administration may be by nasal spray or nasal drops.

The present invention has the advantage over the prior art that it is easier to produce, with retained or improved immunological effect, which in turn allows for more flexible administrative routes.

The present invention also has the advantage that it is easier to purify in a soluble faun and has increased stability in solution.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Figure 1:
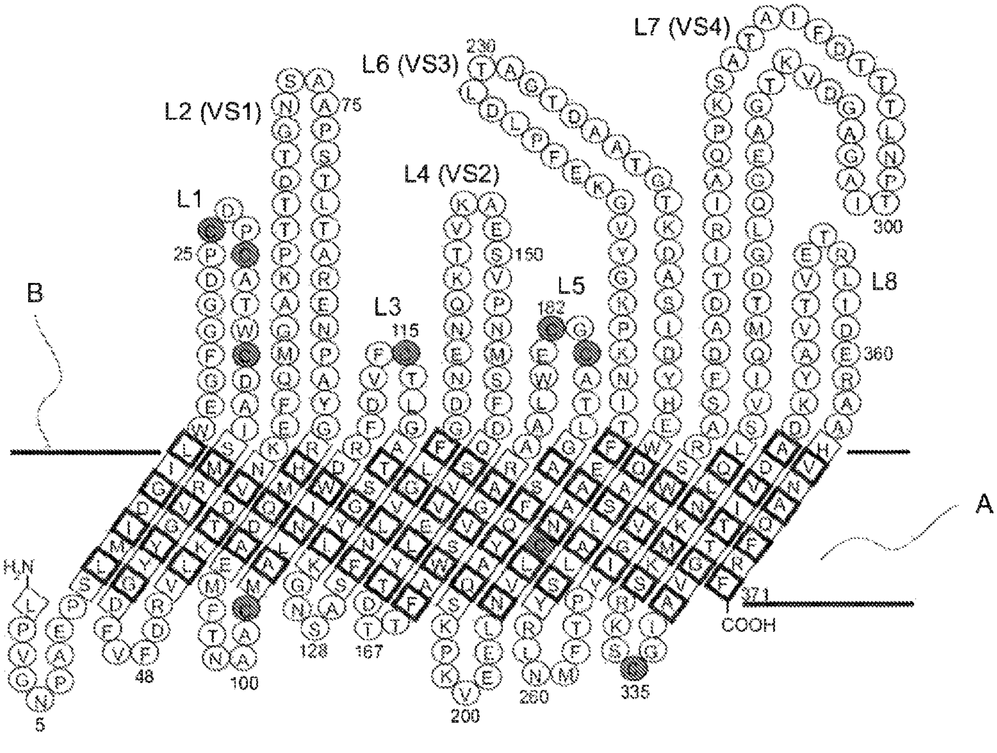
FIG. 1 is a schematic illustration of WT MOMP protein.

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on an embodiment of the present invention applicable to a polypeptide for producing an immune response which is protective against *Chlamydia trachomatis*, and in particular to a chimeric polypeptide, based on the *Chlamydia trachomatis* serovar E polypeptide MOMP, for producing an immune response which is protective against *Chlamydia trachomatis*. However, it will be appreciated that the invention is not limited to this application but may be applied to many other serovars, including for example serovars A to K, Ba, Da, Ia, Ja, L1 to L3, and L2a.

The present inventors have found a chimeric polypeptide, based on the MOMP protein, which functions as an antigen for immunization against *Chlamydia trachomatis*, and yet is easy to purify, due to its relatively small size and reduced hydrophobicity in comparison to WT MOMP protein.

As will be shown in greater detail below, the polypeptide may be expressed in a variety of hosts, such as *Escherichia coli, Ambidopsis thaliana* and *Daucus carota*. However, any kind of host such as bacteria yeast, fungi, plant, insect or mammalian cells may be used for expression. The polypeptide or MOMP chimera, which comprises two loops of the WT MOMP protein, is more water soluble than the WT protein and is optimized regarding antigenicity since it includes T and B lymphocyte—stimulating epitopes, which is important for the immunological effect. Furthermore, it is easier to purify and more stable.

The polypeptide may be administered to a subject by any means known to one of ordinary skill in the art. For example, administration to the human or animal may be local or systemic and accomplished orally, parenterally, by inhalation spray, topically, rectally, nasally, buccally, sublingually vaginally, or via an implanted reservoir. The term “parenteral” as used herein includes subcutaneous, intravenous, intraarterial, intramuscular, intradermal, intraperitoneal, intrathecal, intraventricular, intrasternal, intracranial, and intraosseous injection and infusion techniques.

In an embodiment, a pharmaceutical composition is also provided, said composition comprising an effective amount of at least one polypeptide according to some embodiments and a pharmaceutically acceptable carrier. The composition may be formulated into solid, liquid, gel or suspension form for: oral administration as, for example, tablet (for example, targeted for buccal, sublingual or systemic absorption), bolus, powder, granule, paste or gel for application to the tongue, hard gelatin capsule, soft gelatin capsule, mouth spray, emulsion and microemulsion; parenteral administration by subcutaneous, intramuscular, intravenous or epidural injection as, for example, a sterile solution or suspension; topical application as, for example, a cream, ointment, patch or spray applied to the skin; intravaginal or intrarectal administration as, for example, a pessary, cream or foam; sublingual administration; ocular administration; transdermal administration; or nasal administration, such as nasal spray, or nasal drops.

In an embodiment, the polypeptide may be administered orally to a subject, such as a mouse or a human. In another embodiment, the polypeptide may be administered nasally to a subject, such as a mouse or a human. The nasal administration may be by a spray or by drops. In yet another embodiment, the polypeptide may be administered parenterally to a subject, such as a mouse or a human.

The present inventors found a construct with epitopes according to an embodiment, important for $CD4^+$ T lymphocytes, cytotoxic T lymphocytes (CTL) as well as neutralizing antibodies, which are necessary for the creation of a protective immune response against *Chlamydia trachomatis*. This new protein induced immunogenic response as well as a protective effect in mice.

The type and quantity of amino acid residues separating the epitopes, such as separating SEQ ID NO: 1 and SEQ ID NO: 2, may be selected such, as known in the art, that the polypeptide is easily purified, the corresponding nucleic acid sequence is conveniently expressed in the desired cell type and/or the polypeptide may be administered in a desirable formulation. Preferably, this selection is done such that capacity of the polypeptide for producing an immune response against *Chlamydia trachomatis* is kept high, or at least at an acceptable level.

The designed construct was successfully transferred into the *Arabidopsis thaliana* genome, and stable integration of the transgene was demonstrated over at least six generations which was proved by immunoblot analysis. This is advantageous, since stability of the transgene in the offspring is important for the future possibilities to scale up transgenic plant production. Since *A. thaliana* is eaten raw by mice, it may function as a model system in pre-clinical trials.

Further advantages of using edible transgenic plants for vaccinations include the simple delivery, cost efficiency and possibilities for local production. Moreover, vaccines produced in this way are safe and non-infectious and open up for a possibility to provide a high frequency of boosts. Improvement of administration protocols and use of adjuvants during oral vaccination may increase efficiency of edible vaccines.

Plant-based edible vaccines are good candidates for such immunization. They are safe, cheap, and could be grown locally. In addition, transgenic plants are capable of producing several different antigens by crossing plants producing different products. It is known that transgenic plants can stimulate a two-way immune response, both systemic and mucosal.

Furthermore, the designed construct was successfully transferred into *Escherichia coli*. This is advantageous, since *E. coli* is well known and a commonly used host for protein production.

In an embodiment, the polypeptide is linked to an expression tag, such as a V5 and/or a His tag. This is advantageous, because it simplifies production and purification of the polypeptide.

DETAILED DESCRIPTION OF EMBODIMENTS

The following is a detailed description of embodiments. It is provided for illustrative purposes only, in order for a person skilled in the art to be able to make and use the invention. However, it shall not be construed as limiting in any way.

Chimeric MOMP Construction

Total genomic DNA was isolated from bacterial suspension (Örebro University Hospital, Sweden), emanating from an *Chlamydia trachomatis* serovar E infected patient, using QIAamp® DNA Mini Kit (Qiagen, Hilden, Germany) according to the manufacturer’s protocol. The initial amplification of two DNA fragments (as illustrated by the similar parts VS2 and VS4 in FIG. 1) of *Chlamydia trachomatis* MOMP containing a number of chosen B and T cell epitopes was performed from the prepared genomic DNA using primers according to SEQ ID NOs: 10 to 13 (VS2 forward 1, VS2 back 1, VS4 forward 1 and VS4 back 1, respectively). The PCR reactions utilized Ex Taq DNA polymerase (Takara Bio Inc, Shiga, Japan) and consisted of 35 cycles of 98° C. (10 seconds), 55° C. (30 seconds), and 72° C. (1 min) followed by extension at 72° C. (15 min) The PCR products were purified with QIAquick PCR Purification Kit (Qiagen, Hilden, Germany) and subjected for a second PCR performed under the same conditions as the first PCR with primers according to SEQ ID NOs: 14 to 15 (VS2 forward 2&3 and VS2 back 2, respectively) for VS2 extended fragment and SEQ ID NOs: 16 to 17 (VS4 forward 2 and VS4 back 2&3, respectively) for VS4 extended fragment. The PCR primers for amplifying VS2 and VS4 fragments with the addition of the linker sequence [$(Gly_4Ser)_3$], according to SEQ ID NO: 20, or the linker sequence [$(Gly_4Ser)_2Gly_4$] according to SEQ ID NO: 26, were designed based on the nucleotide sequences of the linker and the chosen MOMP fragments. The purified fragments are provided as SEQ ID NOs: 1 and 2, and are similar to VS2 and VS4 fragments according to FIG. 1. The purified fragments were spliced by overlap extension, known to a person skilled in the art, using the following conditions: 10 cycles of 95° C. (1 min), 55° C. (1 min), 72° C. (2 min), followed by extension at 72° C. for 15 min. The spliced product was used for a third PCR utilized Pfx Taq-polymerase (Invitrogen, Carlsbad, Calif.) and 25 cycles of 94° C. (15 s), 55° C. (30 s), 72° C. (2 min) followed by a single extension step at 72° C. (30 min). The amplification was performed with primers SEQ ID NO: 14 and SEQ ID NO: 17. The obtained PCR product according to SEQ ID NO: 9 was purified as described before.

The purified fragments, SEQ ID NOs: 1 and 2, comprises epitopes for producing an antigen-specific immune response which is protective against *Chlamydia trachomatis*, and parts of the membrane spanning part of the major outer membrane protein (MOMP) of *Chlamydia trachomati*. The membrane spanning part of SEQ ID NO: 1 is represented by amino acid number 22 to 27 and the membrane spanning parts of SEQ ID NO: 2 are represented by amino acid number 3 to 9 and 17 to 23, respectively. An advantage with using only fragments of MOMP is that the polypeptide is easier to produce in purified form compared to the whole MOMP protein. An advantage with the polypeptide comprising parts of the membrane spanning part of MOMP is that the three dimensional structure of the epitopes is conserved. Another advantage with the polypeptide comprising parts of the membrane spanning part of MOMP is that the epitopes are retained in the construct during production. A further advantage with this is that it provides the possibility for hydrophobic interaction between the two parts of the chimera, in turn providing a three dimensional domain that could mimic antigenic features of the whole MOMP protein.

It is believed that the membrane spanning part is a helical conformation.

In an embodiment each of the fragments, such as SEQ ID NOs: 1 and 2, comprises two helices.

This is advantageous, since it further enhances the advantages mentioned above.

Taken together, the polypeptide enables retained or improved antigenicity, while being easy to produce and purify.

In an embodiment, the epitopes for producing an antigen-specific immune response which is protective against *Chlamydia trachomatis* are conserved in several serovars of *Chlamydia trachomatis.*

This is advantageous, since it enables a protective response against more than one serovar of *Chlamydia trachomatis.*

Cloning and Expression of MOMP Chimera in *E. coli*

The purified MOMP chimera was cloned into pET101/D-TOPO® vector using Champion pET Directional TOPO® Expression Kit (Invitrogen, Groningen, The Netherlands) according to the manufacturer's protocol. The confirmation that our construct was in frame with the C-terminal V5 and 6× His fusion tags was done by sequencing (ABI PRISM 310 GeneticAnalyser, Applied Biosystems, Foster City, Calif.). The chimeric protein was expressed in BL21 Star™ (DE3) *E. coli* strain. A volume of 1000 ml of LB medium containing 50 μg/ml carbenicillin and 2.5 mM betaine (Sigma, Steinheim, Germany) was inoculated with 10 ml of a fresh overnight culture derived from a single colony of *E. coli* and grown at 37° C. to an optical density (OD) of 0.72 at 600 nm. Isopropyl β-D-thiogalactoside (IPTG, Invitrogen, Groningen, The Netherlands) was added to final concentration of 0.15 mM, and the culture was incubated for further 4 hours. Bacteria were harvested by centrifugation (5000×g, 15 min) and subjected to protein purification according to Sigma-Aldrich's protocol for their Ni-NTA resin.

Purification of MOMP Chimera

The bacterial pellet was resuspended in lysis buffer (50 mM potassium phosphate, pH 7.8, 400 mM NaCl, 100 mM KCl, 10% glycerol, 0.5% Triton X-100, 10 mM L-histidine, 1 mM phenylmethylsulfonyl fluoride (PMSF)), frozen in liquid nitrogen and then thawed at 42° C. Freezing and thawing were repeated 3 times followed by sonication on ice (35 W, 6×30 seconds) to facilitate lysis. After ultracentrifugation (45000×g, 45 min) two fractions were obtained—a soluble fraction and an insoluble fraction. The soluble fraction was subjected to purification under native conditions using HIS-Select Nickel Affinity Gel (Sigma, Saint Louis, Mo.) according to the manufacturer's protocol. The pellet was resuspended in 0.1 M sodium phosphate pH 8.0, 8M urea and sonicated as described above. Insoluble material was removed by ultracentrifugation (50000×g, 60 min). The supernatant was subjected to purification by immobilized metal-ion affinity chromatography under denaturing conditions according to the manufacturer's recommendations. The collected fractions of eluted protein were pooled together (separately for the native protein and for the denatured protein) and concentrated by Amicon Ultra centrifugal filter device with molecular weight cut off 10 KDa (Millipore, Billerica, Mass.).

DNA Construction for Plant Transformation

The chimeric MOMP was re-amplified from the previously obtained construct using primers SEQ ID NO: 14 and 18 (with introduced STOP codon into the primer according to SEQ ID NO: 18) and Pfx Taq-polymerase (Invitrogen, Carlsbad, Calif.) to produce blunt-end PCR product. PCR was carried out using the following conditions: 35 cycles at 94° C. 15 s, 55° C. 30 s, 72° C. 2 min followed by a single extension step at 72° C. for 30 min The PCR product was purified as described before and used for subcloning into plant expression vector.

As a plant expression vector we used pGreen0229 (www-.pgreen.ac.uk) kindly provided by Dr. P. Mullineaux and Dr. R. Hellens, John Innes Centre and the Biotechnology and Biological Sciences Research Council (Norwich Research Park, UK). The expression cassette contained CaMV35S promoter and CaMV polyA terminator sequences, separated by a multi-cloning site. The vector was linearized by SmaI enzyme at the multi-cloning site and used for cloning of the chimeric MOMP construct. The resulting plasmid was verified by sequencing to confirm correct orientation of the insert (ABI PRISM 310 GeneticAnalyser, Applied Biosystems, Foster City, Calif.).

Plant Transformation in *Arabidopsis thaliana*

The pGreen0229/chimeric MOMP was used to transform *Agrobacterium tumefaciens* (EHA105), kindly provided by E. E. Hood (Department of Biology, Utah State University), by electroporation.

Positive clones were selected on LB media supplemented with kanamycin (50 μg/ml) and tetracyclin (5 μg/ml).

*Arabidopsis thaliana* ecotype Columbia-0 (Col-0) (The European *Arabidopsis* Stock Centre, Loughborough, UK) was used as background for plant transformation. After sowing on a fertilized soil:Perlite:Vermiculite mixture (1:1:1), seeds were maintained for 5 days at 4° C. (darkness) and then transferred to a growth chamber (22° C., 16 h light, 8 h darkness, 70% humidity). The fluorescence rate of white light was 100 μmol photons $m^{-2}$ $s^{-1}$ (PAR). Transgenic plants were produced by the simplified floral dip method of four-week-old *Arabidopsis* plants as known within the art and selected by germination on Murashige and Skog (MS) medium containing glufosinate-ammonium (BASTA) (10 μg/ml) (Riedel-de Haën, Seelze, Germany) and sephatoxime (400 μg/ml) (Sigma, Steinheim, Germany). Resistant plants were transferred to potting mix for analysis, self-pollination and seed production. The seeds obtained from individual plants producing 100% BASTA-resistant progeny were used for further experiments.

Plant Transformation in *Daucus carota*

In an alternative embodiment, the pGreen0229/chimeric MOMP was used to transform *Agrobacterium tumefaciens* (EHA105), kindly provided by E. E. Hood (Department of Biology, Utah State University), by electroporation.

Positive clones were selected on LB media supplemented with kanamycin (50 μg/ml) and tetracyclin (5 μg/ml).

Seeds of *Daticus carota* (carrot) (L.) ssp. sativus cv Napoli F1 (Weibulls tradgard AB, Hammenhög, Sweden) were sterilized in 25% [v/v] chlorine for 45 min and another 2 h in 2.5% [v/v] chlorine, 70% ethanol for 1 min, and, finally, washed three times in water during 1 h. Sterile *D. carota* seeds were germinated on MS medium without growth regulators and callus cells were initiated from excised hypocotyls by cultivation on MS medium with 2,4-dichlorophenoxyacetic acid (1 mg/l). The callus cells were suspended in liquid medium of the same type and grown in darkness on a shaker (90 rpm) at 25° C. For production of somatic embryos, the cells were transferred to a growth regulator-free MS medium. For transformation, carrot cells were taken 10-14 days after addition of fresh growth medium. The carrot cells were packed by centrifugation (at 100 g for 1 min), 4-5 ml packed cells were diluted in liquid MS medium up to 20 ml and 600 μl of *A. tumefaciens* carrying the vector in LB medium (optical density 1.5 at 600 nm) was added. The cells and bacteria were co-cultivated for 3 days in darkness at 25° C. using a shaker (90 rpm). For selection of transgenic carrot cells, they were repeatedly washed three times by centrifugation in liquid MS medium to remove bacteria and were subsequently imbedded and further cultivated in growth regulator-free medium supplemented with BASTA (0, 1, 5, or 10 μg/ml) and cephotaxime (500 μg/ml) in dim light (1 $\mu E/m^2/s$) at 25° C. The density of carrot cells was 0.1-0.9 ml packed cells/10 ml of medium. Growing aggregates, and in some cases plants, were transferred to growth regulator-free MS medium without BASTA. The in vitro plants were cultivated and acclimated in 1 l plastic cans (PhytoTechnology Laboratories, Terrace Lenexa, Kans., USA) in a mist-house for approximately 2 weeks giving 18 h/6 h light/darkness in dim light and, subsequently, cultivated in pots using the equal light period but with a light intensity of 50 $\mu E/m^2/s$.

Immunoblotting

To prepare protein samples, *Arabidopsis* tissues were ground with a mortar and pestle in an extraction buffer containing 50 mM Tris, 8 M urea, 1% Triton X-100 and 1 mM DTT (pH 7.5). Protein extracts were separated by SDS-PAGE and blotted onto nitrocellulose membrane Hybond-C (Amersham Biosciences, Buckinghamshire, England). The membrane was blocked in 3% BSA (Sigma, Steinheim, Germany) in TBS (0.02 M Tris-HCl, 0.15 M NaCl, pH 7.4) for 1 h and probed with mouse monoclonal antibodies to *Chlamydia trachomatis* MOMP (Acris Antibodies Gmbh, Germany) diluted 1:2500 for 1 h. Chimeric MOMP was detected with alkaline phosphatase (AP) conjugated anti-mouse antibody (Promega, Madison, Wis.) and visualized with NBT and BCIP (Promega, Madison, Wis.).

Genomic DNA Extraction and Southern Blot Analysis

Plant genomic DNA was isolated using JETFLEX Genomic DNA Purification Kit (GENOMED GmbH, Lane, Germany), and 15 μg DNA was cleaved with either DraI, NdeI or NotI (Sigma). These enzymes do not cleave the chimeric MOMP sequence. The cleaved DNA was separated by electrophoresis on a 1% agarose gel and transferred to Hybond-N membrane (GE Healthcare). The membrane was probed with chimeric MOMP DNA labelled with $^{32}$P-dCTP using the random primers DNA labelling system (Invitrogen, Carlsbad, Calif.). The number of bands observed on the X-ray film corresponded to the number of T-DNA insertions in the plant genome.

Verification of the Constructed Immunogen

A pilot experiment was performed. Five mice (C57/b16) were immunized by the recombinant MOMP chimera by intranasal administration (i.n.) with 10 days between each priming. The administrated dose was 10 μg of the purified recombinant MOMP chimera. The mice were bled before immunization start, and after each priming, and analysed for serum anti-MOMP chimera IgG by ELISA. ELISA plates (Nunc Maxisorp, Odense, Denmark) were coated with recombinant MOMP chimeric protein (2 μg/ml). Sera were diluted in PBS. Anti-chimera antibodies (Abs) were followed by HRP-labeled rabbit anti mouse Ig Abs and visualized using O-phenylene diamine substrate/0.04% $H_2O_2$ in citrate buffer (pH4.5). The reactions were read spectrophotometrically at 450 nm. The anti-MOMP chimera serum titres $\log_{10}$ titers, showed promising results (data not shown).

Chimeric MOMP Construct and its Over Expression in *E. coli*

Figure 2:
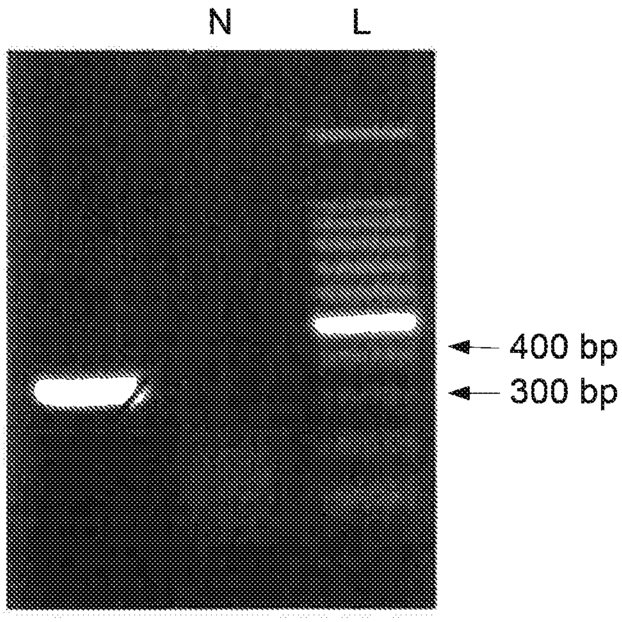
FIG. 2 is a picture of the result of a PCR analysis of a gene construct according to an embodiment.
Figure 3:
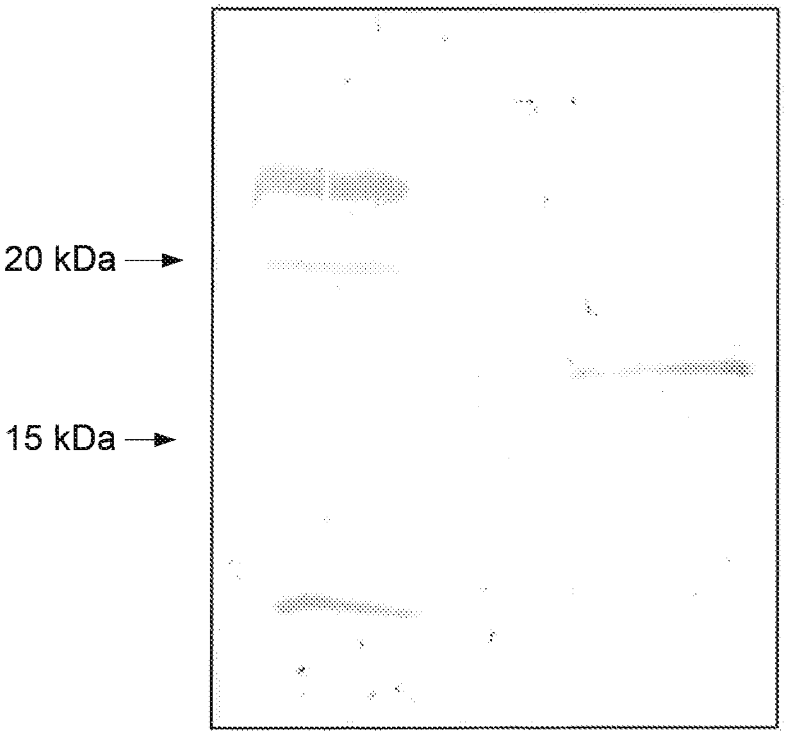
FIG. 3 is a picture of a the result of a Western blot analysis of a polypeptide according to an embodiment.
Figure 4:
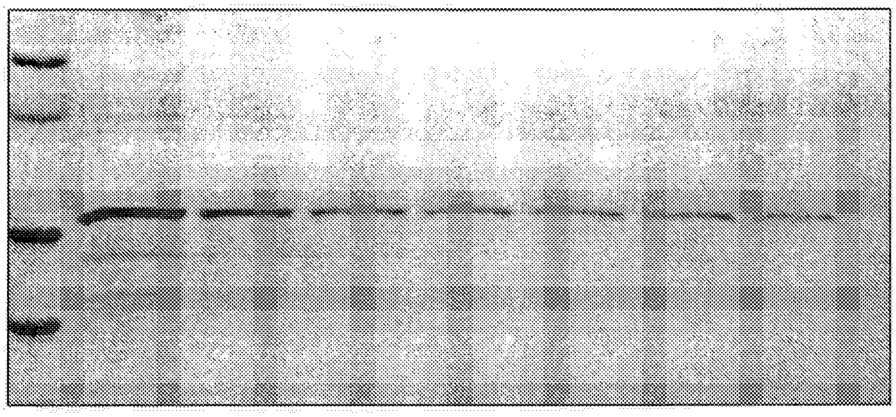
FIG. 4 is a picture of a Coomassie blue staining of purified MOMP protein according to an embodiment.

The reverse and forward primers used in PCR to amplify the VS2 and VS4 variable regions of MOMP for assembling the chimera were designed from the nucleotide sequence data. The sequence according to SEQ ID NO: 19, encoding a common flexible linker, $(Gly_4Ser_3)_3$, according to SEQ ID NO: 20, was introduced into the 5'-end of the primers according to SEQ ID NOs: 14 and 15, respectively. In an embodiment, the sequence according to SEQ ID NO: 25, encoding another common flexible linker, $(Gly_4Ser)_2Gly_4$, according to SEQ ID NO: 26, was introduced into the 5'-end of the primers according to SEQ ID NOs: 14 and 15, respectively. The amplified VS2- and VS4-like fragments (SEQ ID NOs: 1 and 2, respectively) were then assembled in the following direction 5'-SEQ ID NOs: 1: linker: SEQ ID NOs: 2-3'. The produced chimera showed the expected size of 351 bp, as shown by the strong band in the L lane in FIG. 2. FIG. 2 shows the result of PCR analysis of the assembled gene construct. N denotes a negative control of PCR-reaction, L denotes a DNA size marker. The product was verified by sequencing and cloned into pET101 vector. The over-expressed protein was detected by both anti-His Abs (data not shown) and anti- MOMP Abs (Acris Antibodies Gmbh, Germany) as seen in FIG. 3, which shows the results of a Western blot analysis of recombinant chimeric MOMP protein expressed in *E. coli* and purified using Ni-NTA technology. A band of the expected size (17 kD) was detected with mouse monoclonal antibodies to *Chlamydia trachomatis* MOMP (Acris Antibodies Gmbh, Germany). L denotes a protein size marker. We scaled-up expression of the MOMP chimera to 2000 ml bacterial culture for purification using Ni-NTA affinity technology. The purified chimera protein stained with Coomassie Blue is shown in FIG. 4. The protein purified under native conditions was used later in immunization experiments for verification of immunogenic features of the designed construction and for production of anti-MOMP chimera polyclonal antiserum. The protein purified under denatured conditions was used for coating of ELISA plates for detection of specific Abs in mouse sera.

Analysis of Transgene Insertion and Chimera Production in Planta

The designed MOMP chimera was ligated into the SacI cloning site of the pGreen vector, and the sequence of the cloned fragment was verified. The recombinant expression vector was used to transform *A. thaliana* plants of the Col-0 ecotype. Forty transgenic plants were selected after initial seedling screening with bialaphos. Three selected transgenic lines number 9, 15 and 25 were used in further analysis, and stable integration of the transgene for up to sixth generation was demonstrated, as seen in FIG. 4.

Figure 5:
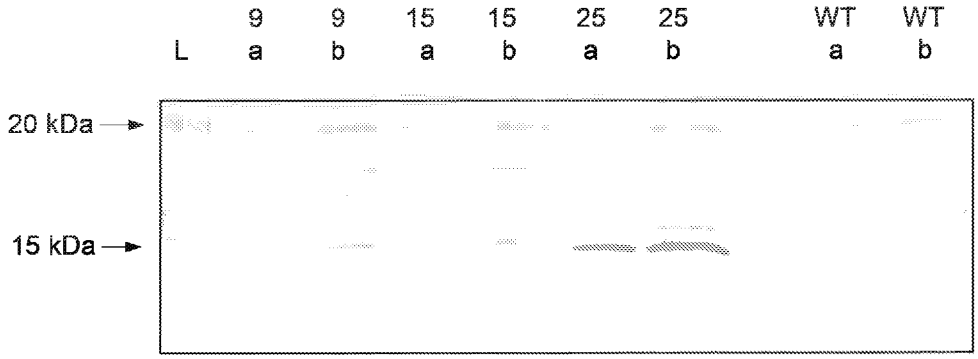
FIG. 5 is a picture of the results of a Western blot analysis of a polypeptide according to another embodiment.

The Western blot detection of constitutively-expressed chimeric MOMP protein in unfractionated leaf extract is shown in FIG. 5: a comparison of the three transgenic lines, in duplicate "a" and "b", with untransformed plants (WT, as a negative control) reveals a specific band of appropriate size which fits well the calculated size of the chimera and the *E. coli* expressed recombinant protein.

Figure 6:
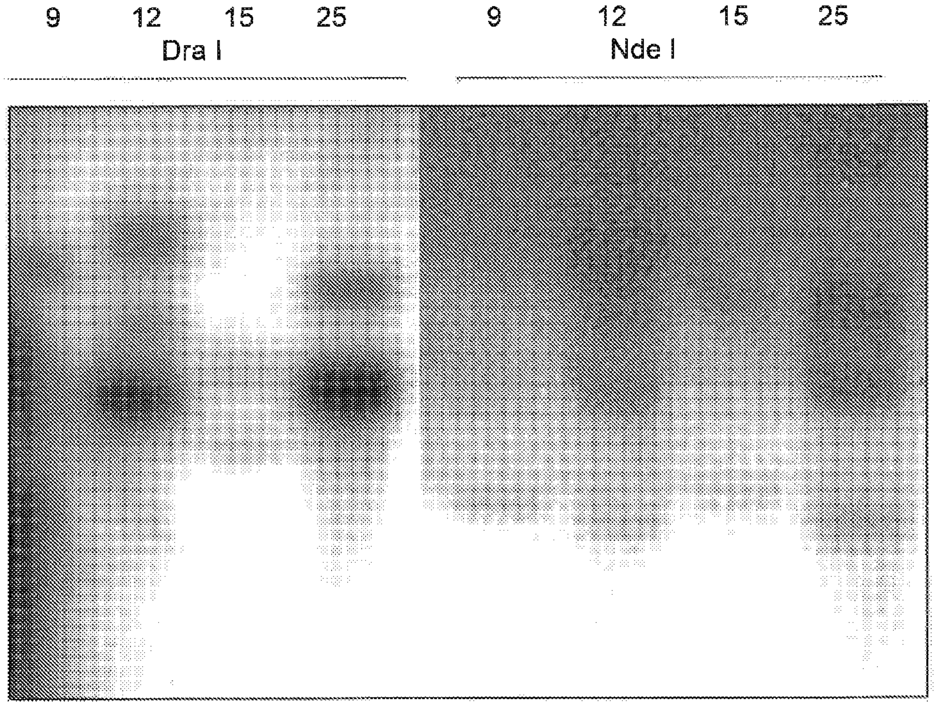
FIG. 6 is a picture of the result of a Southern blot analysis of transformed genomic DNA according to an embodiment.

The chosen transgenic plants were subjected to Southern blot analysis in order to estimate the number of transgenes. Restriction enzymes Dra I, Nde I, and Mlu I were used for cleavage of plant genomic DNA. The results obtained with Dra I and Nde I are shown in FIG. 6. Different numbers of transgene insertions occurred in different lines: line 9 contained one insert, line 12—three, line 15—two, and line 25—four inserts. Although different numbers of the transgene was present in different lines, this did not visually influence the phenotype of the plants. The transformants had an identical morphological appearance compared with the *A. thaliana* wild type (WT) plants.

Figure 7:
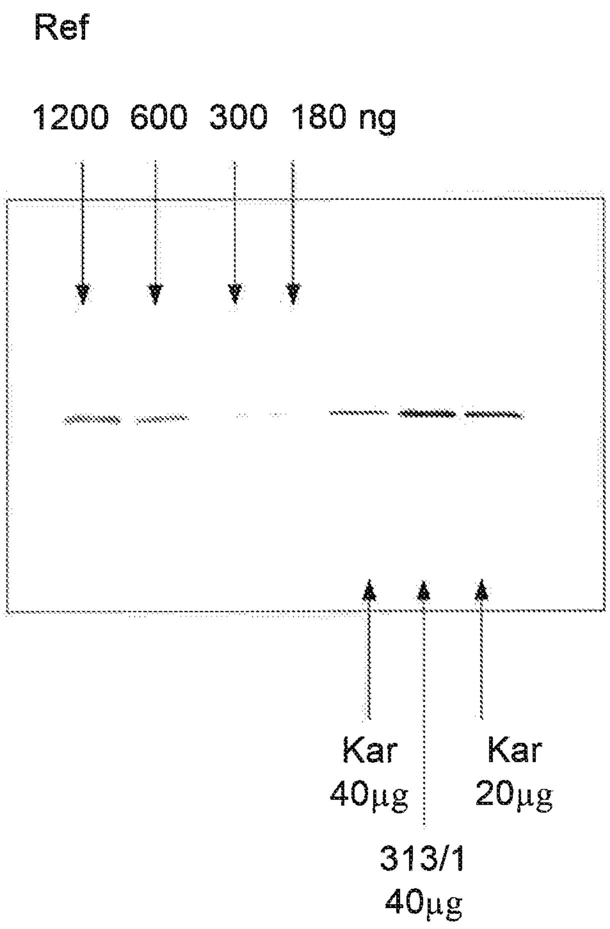
FIG. 7 is a picture of the result of a semi quantification of the polypeptide according to a further embodiment.

The results of the alternative embodiment, using *Daucus carota*, were analysed by grinding about 200 mg carrot root in liquid nitrogen with mortar and pestle. The frozen powder was thawed on ice and vortexed with 200 µl of 50 mM Tris-HCl buffer (pH 7.3) and then analysed as described above. FIG. 7 is shows the results of a semi quantification of the amounts of MOMP chimera produced using *Daucus carota* according to above, with cultivar Karotan (line +; denoted Kar in FIG. 7) and cultivar Napoli (line 313/3; denoted 313/3 in FIG. 7), and comparing to standard amounts of our MOMP chimeric protein (180, 300, 600, and 1200 ng). The line Kar+ produces 450 ng MOMP per 40 µg total soluble protein (TSP), which corresponds to 1%. The line Napoli 313/1 produces 600 ng MOMP per 20 µg TSP, which corresponds to 3%.

Immune Response Induced in Mice by Recombinant Chimeric MOMP Protein with His/V5 Tags Four groups of ten mice were given constructed MOMP chimera according to SEQ ID NO: 6. Administration was conducted according to the following:

A first group was given a mixture of 10 µg purified MOMP chimera and 1 µg cholera toxin (CT) adjuvant, 20 µl intranasally (i.n.) three times with ten day intervals. Ten days after the last administration of MOMP chimera+CT adjuvant, the mice were given a subcutaneous (s.c.) injection with Depo-Provera (Pfizer). Seven days after the Depo-Provera injection, a follow-up administration (boost) of a mixture of 10 µg MOMP chimera+1 µg CT adjuvant, 40 µl was given intravaginally (i.vag).

A second group was given transgenic *Arabidopsis thaliana*, transformed according to above, orally three times with ten day intervals. Each time, mice were given an excess of fresh transgenic *Arabidopsis thaliana* in addition to the regular feed. Ten days after the last administration of transgenic *Arabidopsis thaliana*, the mice were given a subcutaneous (s.c.) injection with Depo-Provera (Pfizer). Seven days after the Depo-Provera (Pfizer) injection, a follow-up administration (boost) of a mixture of 10 µg MOMP chimera+1 µg CT adjuvant, 40 µl was given intravaginally (i.vag).

A third group was given transgenic *Arabidopsis thaliana*, transformed according to above, orally three times with ten day intervals. Each time, mice were given an excess of fresh transgenic *Arabidopsis thaliana* in addition to the regular feed. Ten days after the last administration of transgenic *Arabidopsis thaliana*, the mice were given a subcutaneous (s.c.) injection with Depo-Provera (Pfizer). Seven days after the Depo-Provera (Pfizer) injection, a follow-up administration (boost) of PBS buffer, 40 µl was given intravaginally (i.vag).

A fourth group was used as negative control, i.e. without any administration.

The immune response of the mice was analyzed with ELISA for antigen specific antibodies (IgG and IgA). Next, the strength of the immune response was tested by challenging the mice with *Chlamydia trachomatis* to see if protective immunity, or protective immune response, was obtained. Ten days after the last treatment, blood and vaginal samples were taken. The mice were again treated with Depo-Provera (Pfizer) during seven days and then challenged. Samples of blood and vaginal fluid were taken and analyzed with ELISA as described under "Verification of the constructed immunogene" above. When analyzing immune response in serum and vaginal secretion, immune response was strongest in the first group of mice. The second and third group showed a lower response (some mice were negative). Low levels of antibodies were detectable in vaginal secretion, primarily from mice in the first group.

Figure 8:
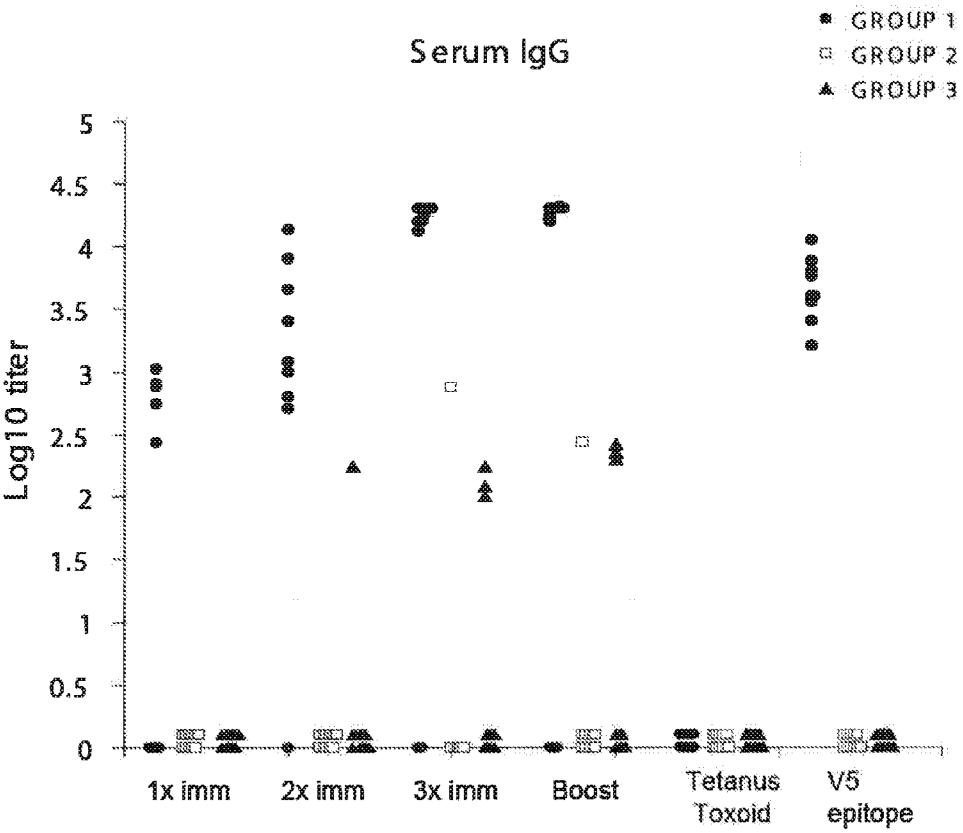
FIGS. 8 and 9 are diagrams showing the results of immunization experiments according to some embodiments.

The results are summarized in FIGS. 8 and 9. FIG. 8 is a graph showing immune response ($\log_{10}$ titer of IgG) for mice in the abovementioned groups one (●), two (□) and three (▲), respectively. The results are sectioned to display (from left to right) immune response after 1 administration, after 2 administrations, after 3 administrations, after 3 administrations plus boost, stimulus by the independent antigen Tetanus toxoid (to make sure that the mice are not hyper-reactive) and stimulus by only V5 epitope. The abovementioned group four (control) did not show any response (data not shown).

Figure 9A:
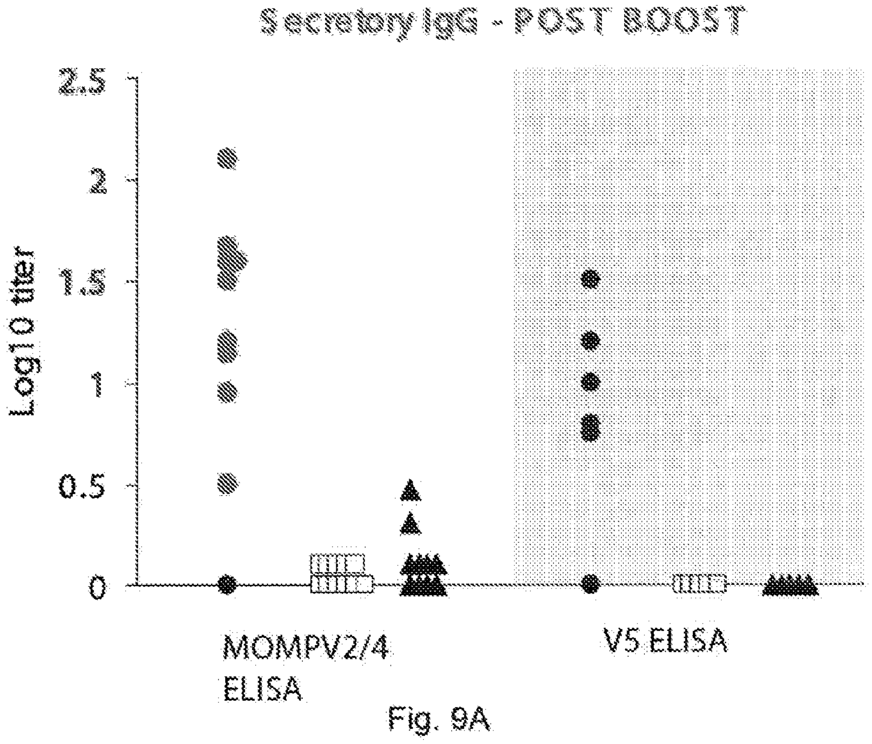
Figure 9B:
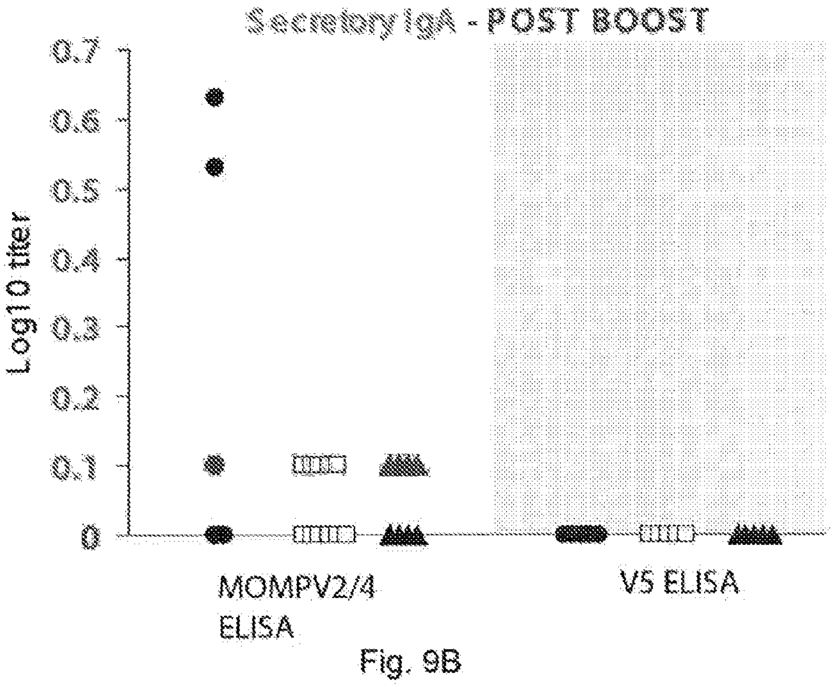
Figure 10:
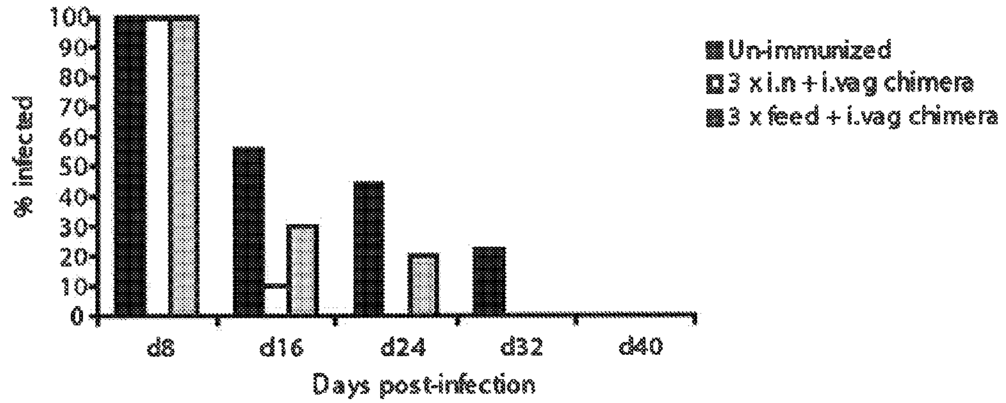
FIG. 10 is a graph showing protective effect of the immunization according to an embodiment, in mice.

FIGS. 9A and 9B are graphs showing immune response (A—$\log_{10}$ titer of IgG; B—$\log_{10}$ titer of IgA) for mice in the abovementioned groups one (●), two (□) and three (▲), respectively. The results are sectioned to display (from left to right) immune response after 3 administrations plus boost as measured with ELISA targeting the MOMP chimera and V5 epitope, respectively. Furthermore, the protective effect caused by immunization with the constructed MOMP chimera was studied in mice, infected by *Chlamydia trachomatis*, serovar D. The results, which are shown in FIG. 10, were measured according to standardized methods, i.e. the number of mice carrying the bacteria 8 (d8), 16 (d16), 32 (d32) and 40 (d40) days after infection, respectively. The black bar represents mice that were not immunized (fourth group), white bar represents mice treated with the MOMP chimera produced in *E. coli* according to above, with intranasal administration and intravaginal boost (first group) and grey bar represents mice treated with the MOMP chimera produced in *Arabidopsis thaliana* according to above, with oral administration and intravaginal boost (second group).

As can be seen, the immunization clearly provides a protective effect. Mice from the first group were partially protected, with faster recovery than the control group.

Immune Response Induced in Mice by Recombinant Chimeric MOMP Protein without His/VS Tags Three groups of ten age-controlled mice were given constructed MOMP chimera according to SEQ ID NO: 3, i.e. without His/V5 tags. Administration was conducted according to the following:

A first group was given a mixture of 10 μg purified MOMP chimera+1 μg CT adjuvant, 20 μl intranasally (i.n.) three times with ten day intervals. Ten days after the last administration of MOMP chimera+CT adjuvant, the mice were given a subcutaneous (s.c.) injection with Depo-Provera (Pfizer). Seven days after the Depo-Provera (Pfizer) injection, a follow-up administration (boost) of a mixture of 10 μg MOMP chimera+1 μg CT adjuvant, 40 μl was given intravaginally (i.vag).

A second group was given PBS buffer 20 μl intranasally (i.n.) three times with ten day intervals. Ten days after the last administration of PBS buffer, the mice were given a subcutaneous (s.c.) injection with Depo-Provera (Pfizer). Seven days after the Depo-Provera (Pfizer) injection, a follow-up administration (boost) of a mixture of 10 μg MOMP chimera+1 μg CT adjuvant, 40 μl was given intravaginally (i.vag).

A third group was used as negative control, i.e. without any administration.

Figure 11:
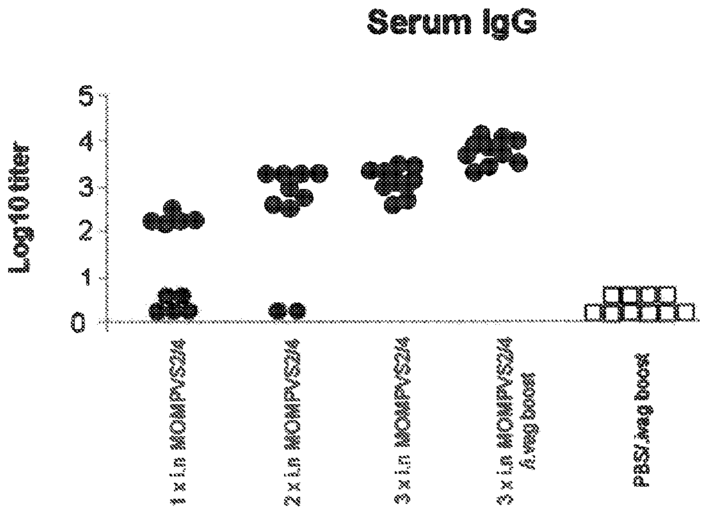
FIG. 11 is a diagram showing the results of an immunization experiment according to an embodiment.

The immune response of the mice was measured by challenging the mice with *Chlamydia trachomatis*. Ten days after the last treatment, blood and vaginal samples were taken. The mice were again treated with Depo-Provera (Pfizer) during seven days and then challenged. Samples of blood and vaginal fluid were taken and analyzed with ELISA as described under "Verification of the constructed immunogen" above. FIG. 11 shows progressively increasing immune response in serum from mice of the first group (black dots) after each administration. Mice from the third group, control, are shown as white squares.

Figure 12:
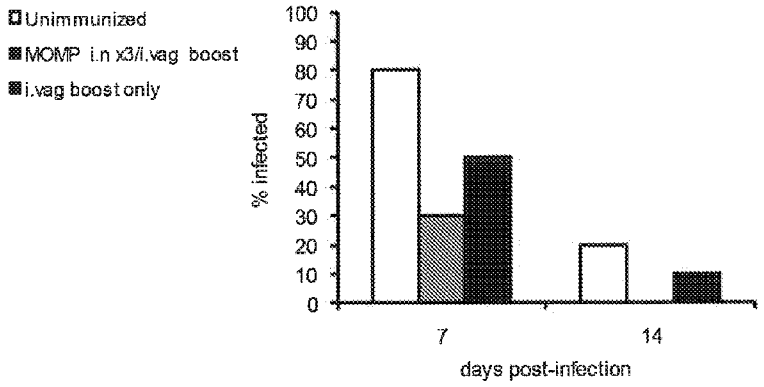
FIG. 12 is a graph showing protective effect of the immunization according to an embodiment, in mice.

The protective effect caused by immunization with the constructed MOMP chimera was studied in mice, infected by *Chlamydia trachomatis*, serovar D. The results, which are shown in FIG. 12, were measured according to standardized methods, i.e. the number of mice carrying the bacteria 7 or 14 days after infection, respectively. The white bar represents mice that were not immunized (third group), grey bar represents mice treated with the MOMP chimera produced in *E. coli* according to above, with intranasal administration and intravaginal boost (first group) and black bar represents mice treated with the MOM) chimera produced in *E. coil* according to above, with intravaginal boost only (second group).

As can be seen, the immunization clearly provides a protective effect.

Fertility Study of Mice Induced with Recombinant Chimeric MOMP Protein without His/V5 Tags In parallel with the immunization study discussed above, a fertility study was performed. Female mice previously immunized by recombinant chimeric MOMP protein according to SEQ ID NO: 3, i.e. without His/V5 tags were further studied in four groups of ten mice in each of the following groups:

A first group was unimmunized and healthy mice.

A second group was unimmunized mice, but infected with *Chlamydia trachomatis*, serovar D.

A third group was mice given a mixture of 10 μg purified MOMP chimera+1 μg CT adjuvant, 20 μl intranasally (in.) three times with ten day intervals. Ten days after the last administration of MOMP chimera+CT adjuvant, the mice were given a subcutaneous (s.c.) injection with Depo-Provera (Pfizer). Seven days after the Depo-Provera (Pfizer) injection, a follow-up administration (boost) of a mixture of 10 μg MOMP chimera+1 μg CT adjuvant, 40 μl was given intravaginally (i.vag). The mice were then challenged with *Chlamydia trachomatis*.

A fourth group was mice given a subcutaneous (s.c.) injection with Depo-Provera (Pfizer). Seven days after the Depo-Provera (Pfizer) injection, a follow-up administration (boost) of a mixture of 10 μg MOMP chimera+1 μg CT adjuvant, 40 μl was given intravaginally (i.vag). The mice were then challenged with *Chlamydia trachomatis*.

All mice were mated and thereafter weighed to identify pregnancy. The pregnant mice were put to death and the number of embryos was countered.

The purpose of the study was to investigate the constructed MOMP antigen's impact on fertility in mice. The numbers of embryos in immunized and non immunized mice challenged with *Chlamydia trachomatis* were compared.

Figure 13:
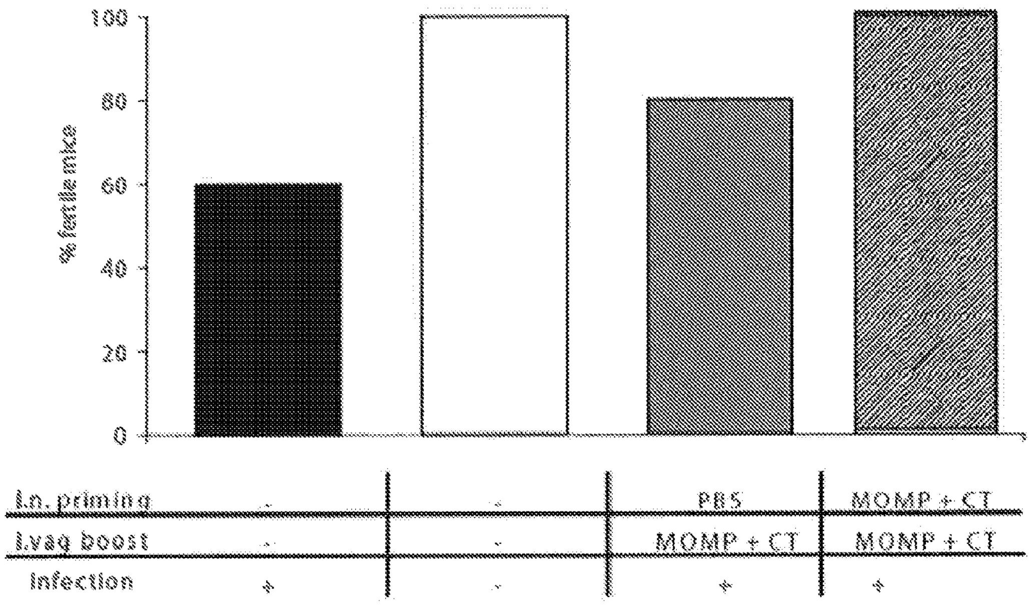
FIG. 13 is a graph showing prohibiting effect of the immunization according to an embodiment, in mice.
Figure 14:
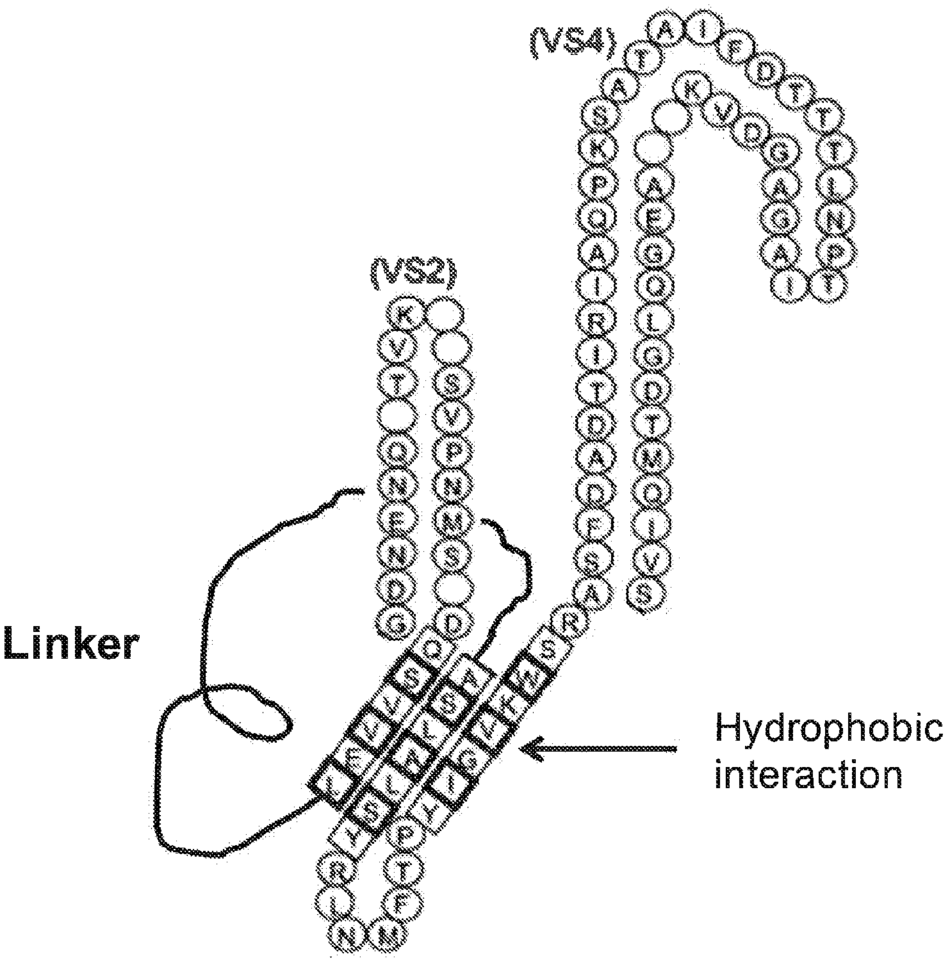
FIG. 14 is a schematic overview of membrane spanning parts according to an embodiment, interacting to form a hydrophobic structure.
Figure 15:
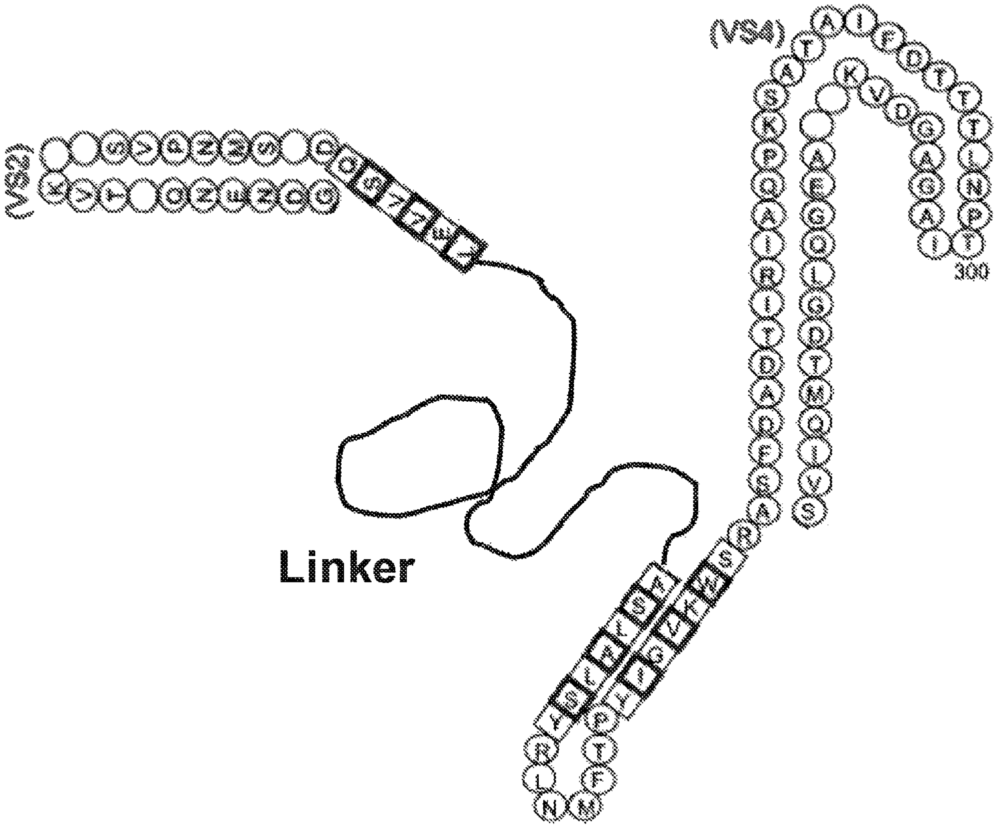
FIG. 15 is a schematic overview of the two parts of the polypeptide according to an embodiment, which move in relation to each other.

The effect is registered as number of mice that produce offspring after they have been infected with *Chlamydia trachomatis*, serovar D and after that mated. As can be seen in FIG. 13, all uninfected and vaccinated mice got pregnant while 40% of the infected females were sterile.

Thus, this study showed that *Chlamydia trachomatis* leads to infertility in 40% of the infected female mice while uninfected mice and mice that have been infected after administration of constructed MOMP chimera according to SEQ ID NO: 3 is 100% fertile. In an embodiment, a method is provided for inducing an immune response protective against *Chlamydia trachomatis* in a mammal, said method comprising administering to said mammal a therapeutically effective amount of the polypeptide according to the first aspect or the compound according to the second aspect or the composition according to the seventh aspect.

In an embodiment, said mammal is a human.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Sequence Listing Free Text

In the sequence listing, the following artificial sequences have free text information:

SEQ ID NO: 4 V5 tag
SEQ ID NO: 5 His tag
SEQ ID NO: 10 VS2 primer, forward 1
SEQ ID NO: 11 VS2 primer, back 1
SEQ ID NO: 12 VS4 primer, forward 1
SEQ ID NO: 13 VS4 primer, back 1
SEQ ID NO: 14 VS2 primer, forward 2&3
SEQ ID NO: 15 VS2 primer, back 2
SEQ ID NO: 16 VS4 primer, forward 2
SEQ ID NO: 17 VS4 primer, back 2&3
SEQ ID NO: 18 VS4 primer, back, STOP
SEQ ID NO: 19 Linker sequence
SEQ ID NO: 20 Linker sequence
SEQ ID NO: 25 Linker sequence
SEQ ID NO: 26 Linker sequence

---

The invention claimed is:

1. An isolated polypeptide comprising a first amino acid sequence which has at least 90% homology with the amino acid sequence according to SEQ ID NO: 1 and a second amino acid sequence which has at least 90% homology with the amino acid sequence according to SEQ ID NO: 2, wherein said first and second amino acid sequences are separated by less than 30 amino acid residues.

2. The polypeptide according to claim 1, wherein the first amino acid sequence has at least 95% homology with the amino acid sequence according to SEQ ID NO: 1 and the second amino acid sequence which has at least 95% homology with the amino acid sequence according to SEQ ID NO: 2.

3. The polypeptide according to claim 1, which is between 107 and 132 amino acids long.

4. The polypeptide according to claim 1, wherein the first amino acid sequence and the second amino acid sequence are separated by a linker according to SEQ ID NO: 20 or SEQ ID NO: 26.

5. The polypeptide according to claim 1, wherein the first amino acid sequence is a sequence according to SEQ ID NO: 21 or SEQ ID NO: 23, and the second amino acid sequence is a sequence according to SEQ ID NO: 22 or SEQ ID NO: 24.

6. The polypeptide according to claim 1 which has at least 90% homology with the amino acid sequence according to SEQ ID NO: 3.

7. The polypeptide according to claim 6, comprising an amino acid sequence according to SEQ ID NO: 3.

8. The polypeptide according to claim 1, fused to an amino acid sequence comprising a His tag according to SEQ ID NO: 5 or a V5 tag according to SEQ ID NO: 4.

9. The polypeptide according to claim 8, having an amino acid sequence according to SEQ ID NO: 6.

10. A compound comprising the amino acid sequence according to claim 1.

11. An isolated nucleic acid which encodes a polypeptide according to claim 1, which has a first nucleic acid sequence which has at least 60% homology with the nucleic acid sequence according to SEQ ID NO: 7 and a second nucleic acid sequence which has at least 60% homology with the nucleic acid sequence according to SEQ ID NO: 8, wherein said first and second nucleic acid sequences are separated by less than 90 nucleic acid residues.

12. The nucleic acid according to claim 11, wherein the first nucleic acid sequence has at least 80% homology with the nucleic acid sequence according to SEQ ID NO: 7 and the second nucleic acid sequence has at least 80% homology with the nucleic acid sequence according to SEQ ID NO: 8.

13. The nucleic acid according to claim 11, comprising a nucleic acid sequence according to SEQ ID NO: 9.

14. A plasmid which comprises the nucleic acid according to claim 11.

15. A cell transformed with an expression vector, wherein the expression vector is a plasmid according to claim 14, the cell being chosen from the group consisting of a plant cell, a bacterium, a yeast cell, a fungal cell, an insect cell or a mammalian cell.

16. A process for producing a polypeptide according to claim 1, which process comprises:

culturing a cell transformed with an expression vector, wherein the expression vector is a plasmid including a nucleic acid including a first nucleic acid sequence which has at least 60% homology with the nucleic acid sequence according to SEQ ID NO: 7 and a second nucleic acid sequence which has at least 60% homology with the nucleic acid sequence according to SEQ ID NO: 8, wherein said first and second nucleic acid sequences are separated by less than 90 nucleic acid residues, the cell being chosen from the group consisting of a plant cell, a bacterium, a yeast cell, a fungal cell, an insect cell or a mammalian cell; and recovering the polypeptide.

17. A vaccine against *Chlamydia trachomatis*, comprising a polypeptide according to claim 1 and a pharmaceutically acceptable carrier.

18. A method of prohibiting infertility in a subject resulting from infection with *Chlamydia trachomatis*, comprising administering a polypeptide according to claim 1 to a subject in need thereof.

19. A method of treating a person infected with *Chlamydia Trachomatis*, comprising: administering a composition that includes a polypeptide according to claim 1.

20. The method according to claim 19, wherein administering the composition comprises oral, parenteral, spray inhalation, topical, rectal, nasal, buccal, sublingual, or vaginal administration.

* * * * *